US011541165B2

(12) United States Patent
Constuble et al.

(10) Patent No.: US 11,541,165 B2
(45) Date of Patent: *Jan. 3, 2023

(54) DRIP CHAMBER ASSEMBLY THAT FUNCTIONS IRRESPECTIVE OF ORIENTATION

(71) Applicant: MOBILE I.V. SYSTEMS, LLC, Chugiak, AK (US)

(72) Inventors: Dale L. Constuble, Helendale, CA (US); Fred Vreeman, Chugiak, AK (US)

(73) Assignee: MOBILE I.S. SYSTEMS, LLC, Chugiak, AK (US)

( * ) Notice: Subject to any disclaimer, the term of this patent is extended or adjusted under 35 U.S.C. 154(b) by 345 days.

This patent is subject to a terminal disclaimer.

(21) Appl. No.: 16/694,917

(22) Filed: Nov. 25, 2019

(65) Prior Publication Data
US 2020/0093983 A1 Mar. 26, 2020

Related U.S. Application Data

(63) Continuation of application No. 15/537,189, filed as application No. PCT/US2015/030947 on May 15, 2015, now Pat. No. 10,485,921.

(60) Provisional application No. 62/093,088, filed on Dec. 17, 2014.

(51) Int. Cl.
*A61M 5/14* (2006.01)
*A61M 1/36* (2006.01)

(52) U.S. Cl.
CPC ........ *A61M 5/1411* (2013.01); *A61M 1/3627* (2013.01)

(58) Field of Classification Search
CPC .................................................. A61M 5/1411
USPC ........................................................ 604/251
See application file for complete search history.

(56) References Cited

U.S. PATENT DOCUMENTS

| | | | |
|---|---|---|---|
| 1,112,168 A | * | 9/1914 | Stilling ............... A61M 5/1411 604/251 |
| 2,113,060 A | | 4/1938 | Sandberg |
| 2,664,085 A | | 12/1953 | Ryan |
| 3,340,871 A | * | 9/1967 | Jellies ............... A61M 5/16886 D24/117 |
| 3,471,349 A | | 10/1969 | Cohen et al. |
| 3,744,492 A | | 7/1973 | Leibinsohn |
| 3,776,229 A | | 12/1973 | McPhee |
| 4,013,072 A | | 3/1977 | Jess et al. |
| 4,126,558 A | | 11/1978 | Luceyk |
| 4,143,659 A | | 3/1979 | Biedermann et al. |
| 4,150,673 A | | 4/1979 | Watt |

(Continued)

FOREIGN PATENT DOCUMENTS

| | | |
|---|---|---|
| CN | 102526844 A | 7/2012 |
| CN | 203577049 U | 5/2014 |

(Continued)

OTHER PUBLICATIONS

Office Action for EP Application No. 15870494.0, dated Jan. 24, 2020.

(Continued)

*Primary Examiner* — Manuel A Mendez
(74) *Attorney, Agent, or Firm* — Dorsey & Whitney LLP

(57) ABSTRACT

A drip chamber assembly that functions irrespective of its orientation and in the presence of increased internal pressure is provided.

22 Claims, 6 Drawing Sheets

(56) References Cited

U.S. PATENT DOCUMENTS

| | | |
|---|---|---|
| 4,214,883 A | 7/1980 | Collier et al. |
| 4,395,260 A | 7/1983 | Todd et al. |
| 4,601,712 A | 7/1986 | Cole et al. |
| 4,892,524 A | 1/1990 | Smith |
| 4,906,260 A | 3/1990 | Emheiser et al. |
| 4,925,451 A | 5/1990 | Amendolia |
| 4,978,337 A | 12/1990 | Theeuwes |
| 5,102,400 A | 4/1992 | Leibinsohn |
| 5,423,346 A | 6/1995 | Daoud |
| 5,569,208 A | 10/1996 | Woelpper et al. |
| 5,575,779 A | 11/1996 | Barry |
| 5,776,109 A | 7/1998 | Urrutia |
| 5,779,674 A | 7/1998 | Ford |
| 5,830,185 A | 11/1998 | Block, Jr. |
| 5,897,526 A | 4/1999 | Vaillancourt |
| 6,261,267 B1 | 7/2001 | Chen |
| 6,347,711 B1 | 2/2002 | Goebel et al. |
| 6,537,356 B1 | 3/2003 | Soriano |
| 6,673,045 B1 | 1/2004 | Kraus |
| 7,279,031 B1 | 10/2007 | Wright |
| 7,700,213 B2 | 4/2010 | Luo et al. |
| 7,736,383 B2 | 6/2010 | Bressler et al. |
| 7,736,384 B2 | 6/2010 | Bressler et al. |
| 7,892,204 B2 | 2/2011 | Kraus |
| 8,523,829 B2 * | 9/2013 | Miner ............... A61M 5/1411 604/126 |
| 8,632,624 B2 | 1/2014 | Cassidy |
| 9,078,981 B2 | 7/2015 | Subramaniam et al. |
| 9,533,109 B2 | 1/2017 | Bryan |
| 9,808,566 B2 | 11/2017 | Gronau et al. |
| 10,485,921 B2 * | 11/2019 | Constuble ............ A61M 5/1411 |
| 2002/0029021 A1 | 3/2002 | Bormann. et al. |
| 2003/0040707 A1 | 2/2003 | Kappel |
| 2004/0254542 A1 | 12/2004 | Sacco |
| 2006/0135939 A1 | 6/2006 | Brown et al. |
| 2006/0189946 A1 | 8/2006 | Adams |
| 2014/0358080 A1 | 12/2014 | Bryan |
| 2017/0340812 A1 | 11/2017 | Berg et al. |

FOREIGN PATENT DOCUMENTS

| | | |
|---|---|---|
| CN | 203777404 U | 8/2014 |
| CN | 106421967 A | 2/2017 |
| DE | 966756 C | 9/1957 |
| DE | 2834588 A1 | 2/1980 |
| DE | 4142625 A1 | 4/1993 |
| DE | 19516493 A1 | 11/1996 |
| EP | 3342437 A1 | 7/2018 |
| GB | 1251461 A | 10/1971 |

OTHER PUBLICATIONS

English translation of Second Office Action received in CN Application No. 201580076234.7 dated Apr. 9, 2020.

Office Action with English Summary for IL Application No. 278508, dated May 23, 2021.

Extended European Search Report; EP Application No. 15870494.0 dated Jun. 7, 2018.

First Office Action dated Jun. 17. 2019 received in CN Application No. 2015800762347.

International Search Report and Written Opinion from International Application No. PCT/US2015/030947 dated Aug. 28, 2015.

* cited by examiner

SECTION A-A

DETAIL B
SCALE 8 : 1

_US 11,541,165 B2_

DRIP CHAMBER ASSEMBLY THAT FUNCTIONS IRRESPECTIVE OF ORIENTATION

CROSS-REFERENCE TO RELATED APPLICATION(S)

This application is a continuation of U.S. application Ser. No. 15/537,189 filed Jun. 16, 2017, which is a U.S. National Stage application of PCT Application No. PCT/US2015/030947 filed May 15, 2015, which claims the benefit of U.S. Provisional Application No. 62/093,088 filed Dec. 17, 2014, which are hereby expressly incorporated by reference, in their entirety, for any purpose.

FIELD OF THE INVENTION

The present invention relates to the field of medicine, and more particularly, to medical devices for fluid delivery to patients or to target devices. More specifically, the invention relates to a drip chamber assembly to be used as part of an infusion apparatus.

BACKGROUND

Intravenous (IV) therapy allows fluids to be infused directly into a vein.

Compared to other fluid administration methods, IV therapy is one of the most efficient ways to deliver fluids to a patient. For infusion, a drip chamber is typically connected to the bottom of an IV bag contacting the fluid to be administered. Tubing is connected to the bottom of the drip chamber and can include means for intravenously inserting a needle or port though which the fluid is administered. The drip chamber permits gas (such as air) to escape from the fluid before the fluid enters a patient. In a patient, the inadvertent introduction of a gas bubble into a vein can result in what is called an embolism, which can in turn produce a blockage in a blood vessel. Many examples of the use of drip chambers by medical personnel to regulate the flow of intravenous fluids to a patient are known and disclosed in U.S. patents (see, e.g., U.S. Pat. Nos. 4,395,260, 4,601,712 and 5,776,109).

The use of a drip chamber also allows an estimate of the rate at which fluids are administered. For a fluid of a given viscosity, drips from a hole of known size will be of nearly identical volume and the number of drips in a minute can be counted. The rate of flow can be controlled, e.g., by a clamp on the infusion tubing. The clamp affects the resistance to flow, and provides increased pressure within the cup. However, other sources of resistance (e.g., whether the patient's vein into which fluids are being delivered is kinked or compressed by the patient's position) cannot be so directly controlled, and a change in position may change the rate of flow leading inadvertently to either too rapid or too slow infusion. In problematic cases such as this, an infusion pump or pressurized infuser may be used which gives a more accurate measurement of flow rate.

In order to minimize the possibility of introducing gas bubbles, and maintain the correct "head height" (typically 39" to 42") for gravity infusion, plus avoid backward flow through the line, it is preferable to keep the drip chamber and infusion apparatus elevated over the patient. However, in emergency situations it is not always possible and/or convenient to keep the drip chamber and infusion apparatus elevated over the patient. Another problem that can occur is that the drip chamber can open up when under pressure resulting from resistance provided by clamping to control drip rate or by vein compression.

Therefore, there is a need for a drip cup assembly which can function consistently, from any position, in any situation, and which can withstand increased internal pressure.

SUMMARY OF THE INVENTION

It has been discovered that a drip chamber assembly is able to hold its connection under pressure when its components utilize complementary locking portions.

This discovery has been exploited to provide, in part, a drip chamber assembly that includes an approximately half-spherical drip chamber bottom, an approximately half-spherical drip chamber top, fluid delivery tubes, and a drip chamber cap. The drip chamber bottom is configured for receiving and interlocking with the drip chamber top having a raised fill line. The interlocking of the half spheres allows the drip chamber to remain joined together even when substantial force is applied within the drip chamber assembly. The interlocking uses a circular portion on the lower portion of the drip chamber top as the male member. The male member is positioned between an outer an inner circular portion (female member) of the upper portion of the drip chamber bottom.

The assembly functions irrespective of its orientation. The fluid that passes through the assembly can be sent directly to a patient or alternatively to a target device. The assembly can be used with a cuff that holds the fluids to be delivered and can use a gas cartridge for pressurizing the cuff, which in turn pressurizes the source of the fluids to provide for rapid delivery or infusion.

In addition, the disclosure provides a drip cup assembly with chamber caps that have outlets with different cross sectional areas. As the cross sectional area of the outlet decreases the number of drops per volume of fluid increases.

Other aspects and advantages of the invention will be apparent from the following description and the appended claims.

BRIEF DESCRIPTION OF THE DRAWINGS

The foregoing and other objects of the present disclosure, the various features thereof, as well as the disclosure itself may be more fully understood from the following description, when read together with the accompanying drawings in which.

DETAILED DESCRIPTION OF PREFERRED EMBODIMENTS

The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

Unless defined otherwise, all technical and scientific terms used herein have the same meaning as commonly understood by one of ordinary skill in the art to which this disclosure belongs. The initial definition provided for a group or term herein applies to that group or term throughout the present specification individually or as part of another group, unless otherwise indicated.

Drip Cup Assembly

The present disclosure provides a drip chamber assembly useful for delivery of fluids either to a patient via intravenous administration or to a target device, both of which benefit from delivery of air-free fluids. The drip chamber of the present disclosure has a spherical design that makes this device an "all position drip chamber" (APDC). This drip chamber prevents air from entering the fluids that are delivered to a patient or target device irrespective of the orientation of the drip chamber assembly. With regard to IV delivery, this feature is useful, e.g., when there is no room and/or time to elevate the fluids or this not sufficient personnel present to hold the fluids over a patient. An advantage of the APDC is that the spherical shape allows for the entire IV tube set up to be stored or transported in any position, whereas a conventional drip chambers needs to be orientated in the vertical position.

In some cases, the APDC is used to deliver a fluid to a target device. The target device can, for example, be an intermediate measuring container. Such a measuring container can include a motor and controller for moving a syringe to deliver the desired amount of fluid. Alternatively, the target device can be some sort of processing device in which further adjustments are made to the fluid before or instead of being delivered to a patient.

The APDC can be used anywhere air or gas needs to be removed from flowing liquid. The APDC incorporates novel closure features to prevent excess pressure within the device from separating the assembly device into its component parts. In addition, the APDC can include a fill line for correct fluid measurement. The fill line can optionally be raised internally and externally, allowing the person administering treatment to the patient or administering fluids to a target device to feel the line. Representative, non-limiting fluids which can be delivered to a patient or target device include glucose solutions, saline solutions, medications in liquid form, aqueous physiologically-acceptable fluids, and blood or plasma.

Figure 1:
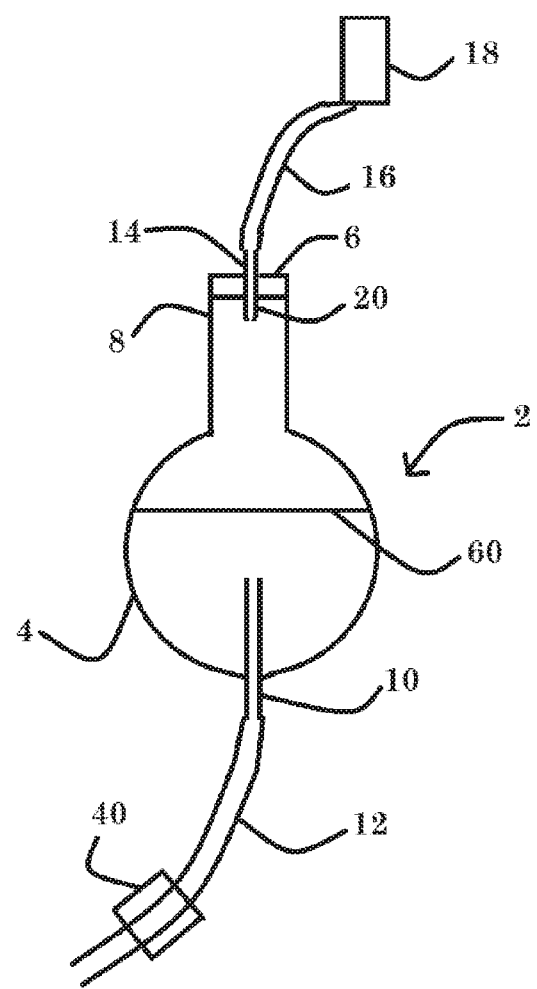
FIG. 1 is a schematic representation of a representative drip chamber assembly.

Referring to FIG. 1, in one aspect, the present disclosure is directed to a drip chamber assembly (2) that includes a joined (hip chamber (4) (i.e., joined from a drip chamber bottom and top (see FIG. 2 and FIG. 3)) and a drip chamber cap (6). The joined drip chamber includes a first distal inlet (8) engaged with the drip chamber cap and a first proximal outlet (10) configured for attaching to a first tube (12) to deliver fluids to a patient. The first proximal outlet extends into at least a portion of the joined drip chamber. The drip chamber cap includes a second distal inlet (14) configured for attaching to a second tube (16) connected to a source of the fluids (18) and a second proximal outlet (20) configured for dripping the fluids into the joined drip chamber. As the cross sectional area of the second proximal outlet decreases the number of drops per volume of fluid increases. For example, the number of drops per mL could increase from 10 to 60 drops per mL if the cross sectional area of the second proximal outlet were to decrease. The incoming fluid enters through the drip chamber cap, fills the joined drip chamber to the fill line (60) and exits through the bottom. The joined drip chamber being spherical in shape, and having the first proximal outlet at the bottom center of the joined drip chamber, ensures that the outlet is continuously submerged in fluid, thus removing air bubbles. The drip chamber assembly of the present invention prevents air from entering the fluids that are delivered to a patient irrespective of the orientation of the drip chamber assembly. This feature is particularly valuable when there is no room and/or time to elevate the fluids or this not sufficient personnel present to hold the fluids over a patient.

Figure 2:
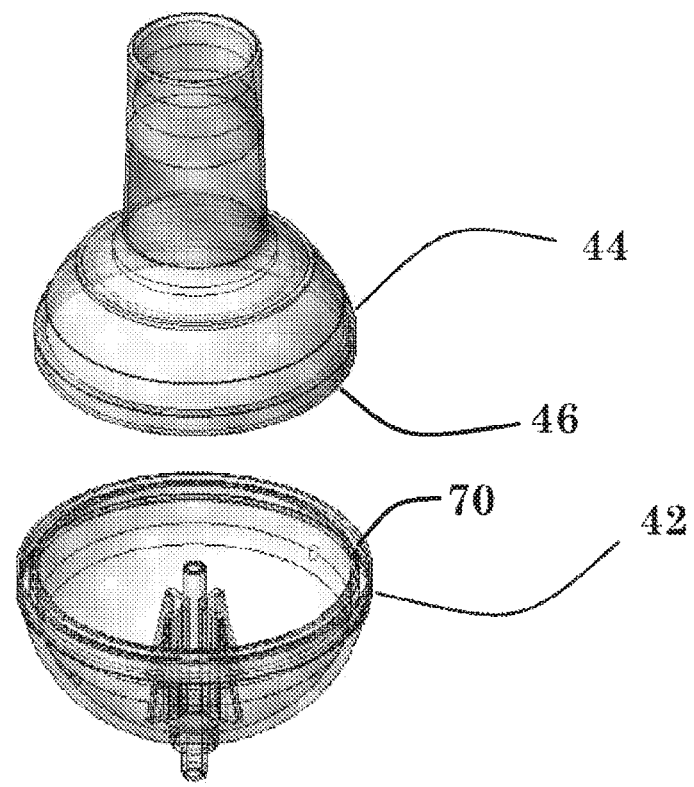
FIG. 2 is a schematic representation of a drip chamber top and bottom.
Figure 3:
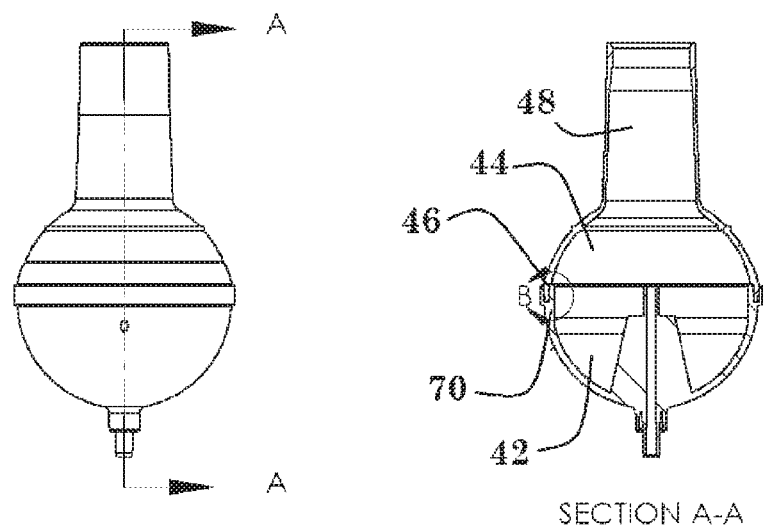
FIG. 3 is a schematic representation of male and female members of the drip chamber top and bottom.
Figure 3:
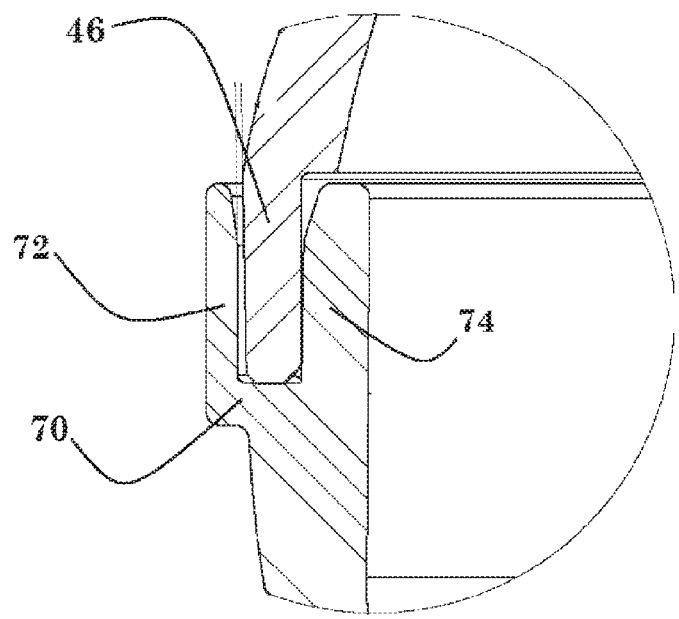

Referring to FIG. 2, the ADPC includes a drip chamber top (44) which consists of two portions: approximately one-half of the spherical portion of the all position drip chamber; and the neck portion which is cylindrical in shape and also acts as the primer pump in the device. This chamber can also have an oblong or polygonal shape to allow for semi-equidistance from the perimeter to the center orifice, providing for continuous immersion of the orifice within. The drip chamber top attaches to the drip chamber bottom (42) and the drip chamber cap (6). The drip chamber top can be made from a flexible plastic, but can be some other polymer or material depending upon the intended use; this could also be accomplished using semi-rigid materials, or a combination of rigid and flexible materials. For example, for medical applications, the drip chamber top can be made from a medical grade flexible PVC, or soft durometer polyurethane, or any flexible thermoplastic approved for the intended application. A flexible top allows for this portion to be squeezed and function as a priming pump for the liquid that flows through the drip chamber, and/or to assist in purging air from the line; if not intended for medical use the chamber could have a sealable vent to allow for purging air or gasses, via a manual or automatic method.

As mentioned above, another feature of the drip chamber top is a raised fill line (60) indicator. This raised fill line enables the operator of the device to physically feel the level to which the chamber is filled. This feature is particularly useful when visibility is low and the operator is in a high pressure hectic situation.

Yet another feature of the drip chamber top is a circular male member (46) located in the lower portion of the drip chamber top. The male member of the interlocking design is further illustrated in FIG. 3. This feature locks the drip chamber top and bottom together such that when pressure is applied to the neck portion (48) the top and bottom will not separate causing leakage.

The drip chamber bottom (42) forms the approximately other half of the ADPC. The drip chamber bottom attaches to the drip chamber top and is one-half to two-thirds spherical, or oblong, or polygonal in shape. For medical applications, the drip chamber bottom can be made from a medical grade acrylic, or any suitable hard plastic or polyurethane. The bottom can be machined from plastic or metal.

A feature of the drip chamber bottom is that it has an exit passage on the center of the sphere that enables the operator of the device to use the chamber in any position while maintaining the exit passage fully submerged in fluid. Another feature of the drip chamber bottom is the female portion (70) (FIG. 3), which includes an outer (72) and inner circular portion (74), that are located in the upper portion of the drip chamber bottom. The circular male member (46) is positioned between the circular outer (72) and inner (74) portions of the female portion (70). This feature is critical for locking the drip chamber top and bottom together in a way that when pressure is applied to the neck portion the top and bottom will not separate causing leakage.

The drip chamber top and bottom can be produced by any type of molding/casting/machining process that can achieve a usable part that interfaces properly with its mating components. These processes include, but are not limited to, injection molding, polyurethane casting, silicone molding, or Soft Cast TPU (thermoplastic polyurethane) methods.

Figure 4:
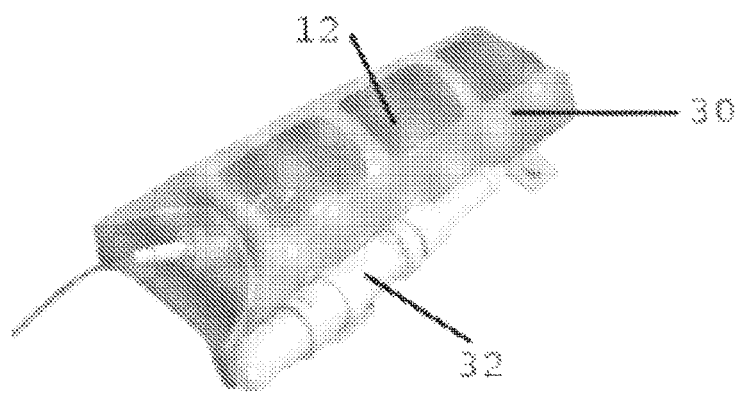
FIG. 4 is a schematic representation of a cuff and carbon dioxide cartridge for use with the drip cup assembly.

Referring to FIG. 4, in another embodiment, the drip chamber assembly can be used with a cuff (30) to hold the source of the fluids (112). A carbon dioxide or other gas cartridge (32) can be used to pressurize the cuff, which pressures the source of the fluids to provide for rapid infusion. The fluid bag is inserted into the cuff, which is inflated, putting pressure on the contents of the IV bag.

The APDC assembly may be put together by attaching the drip chamber top to the drip chamber bottom with the mating areas being the trough interface design discussed above. The parts can be attached using various methods including, but not limited to, solvent bond, ultraviolet (UV) activated glue, sonic welding, over molding, spin welding, and chemical bonding.

The drip chamber cap (6) (FIG. 1) is connected to the APDC top by creating a "slip fit" between the cap and the cylindrical/neck portion of the top. Once this fit is achieved the two components are bonded together further. Bonding methods can include, but not limited to, gluing, ultra violet light-cured bonding, overmolding, or any other secondary process by which two dissimilar plastics can bond together to prevent leaks. There is no glue in the orifice in the center of the drip chamber bottom or cap.

Pressure Testing

Figure 5:
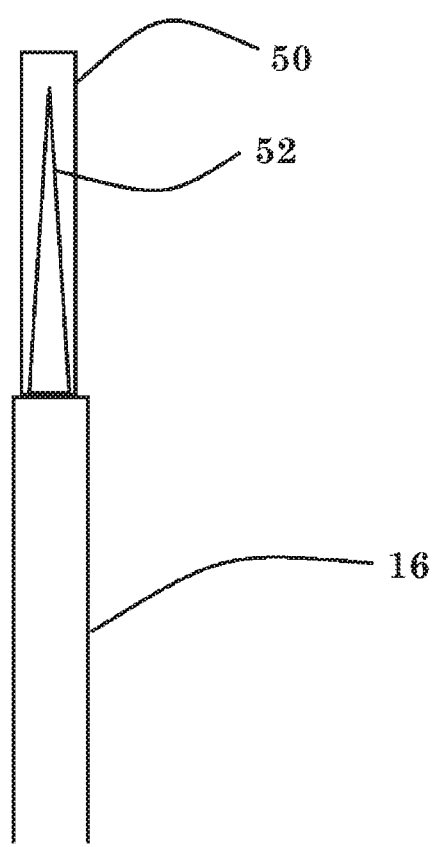
FIG. 5 is a schematic representation of the portion of the drip chamber assembly that gets inserted into an IV bag.
Figure 6:
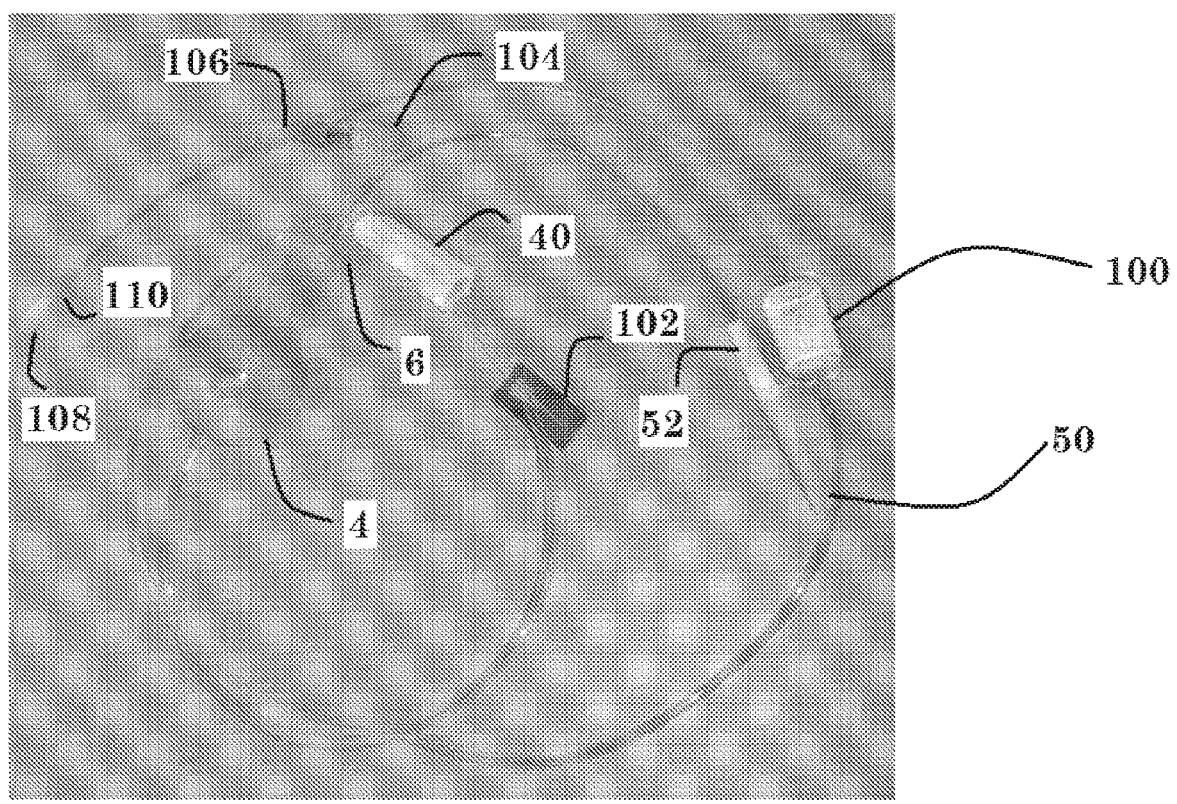
FIG. 6 is a photographic representation of a representative drip chamber assembly with accessories.

In order to determine if there is an air leak in the drip cup assembly, including its attached tubing, testing can be performed by first verifying an air pressure of 50 kpa (or some other designated pressure) on a pressure gauge. Referring to FIG. 5 and FIG. 6, the cap (50) is removed from the spike (52), and the vented female cap (108) is removed from the male leer lock (110) (FIG. 6). The spike and male luer lock are inserted into ports of a testing fixture. The air eliminating filter or "aquaphobic filter" (100) is placed in between the clamps (40, 102) and clamp IV tubing, and the pressure is turned on. The APDC top is squeezed at both glue lines (cap and bottom) to ensure no separation and proper gluing while making sure proper pressure is being kept. Also, the roller clamp (40) and slide clamp (102) are examined to make sure they are open and that injection ports (104), (106), (FIG. 6) are tight. The device is tested to verify that it retains a pressure of 50±0.1 kpa.

APDC air leak testing is performed using a method similar to that used in the tube assembly air leak testing. First, air pressure of 100 kpa (or some other designated pressure) on a pressure gauge is verified. The APDC is corrected to the spike attachment and to male luer lock attachment before the pressure is turned on. The APDC top is then squeezed at both glue lines (cap and bottom) to ensure no separation and proper gluing while making sure proper pressure is being kept. Verification is done to make sure that the device retains a pressure of 100±0.1 kpa.

Tube set assembly bubble leak testing can be performed by first verifying an air pressure of 50 kpa (or some other designated pressure) on a pressure gauge. The cap is removed from the spike and the vented female cap for male luer lock. The spike and male luer lock are then inserted into ports of a testing fixture. The tube on both sides of the air eliminating filter are clamped off. The device is immersed in a water bath where the pressure test is conducted. Air may only leak bout of the filter.

Tube set tensile testing can be performed by clamping the spike to a clean room ceiling and hanging a minimum of 15 N weight to the end of tube assembly for 15 seconds. Each possible joint on the tube assembly is placed into the tensile tester and pulled until failure. Each joint tested can only break at least at 15N or higher.

Instructions for Use

To use the drip cup assembly of the present disclosure to deliver a fluid, the second tube (12) is clamped with roller clamp (40) 6 to 8 inches below bottom of drip chamber shown in FIG. 1. The cover (50) is removed from the spike (52) (FIG. 5). The spike is inserted into the source of the fluids. The source of the fluids can then be inserted into the cuff (30) (FIG. 4). The pressure infuser (32) (FIG. 4) is then activated by screwing the cap that contains the CO2 cartridge clockwise until the cartridge is punctured expelling the gas into the expansion chamber. The roller clamp is released while inverting the drip chamber bottom. The drip chamber is allowed to fill to the indicated fill line (111) and then may be orientated to any position to function properly. The fluids entering the chamber are allowed to reach the fill line. The roller clamp is reclamped adjusting for the desired flow rate.

Inside the drip chamber, fluid should be visible dripping down from the IV bag into the tubing so that the speed of a manual IV setup can be measured. An attendant can view the chamber and count the number of drops per minute. For example, if 25 drops fell over the period of 60 seconds, the IV would be infusing at a rate of 25 drops per minute, or 25 gtt/min. Counting can be done for less than a minute to extrapolate the number of drops that would fall in a full minute.

The drip chamber in use should contain fluid to the raised fill line (111) (FIG. 6). This is because if the drip chamber is too full, the drops will not be visible to count and the rv infusing rate cannot be determined, and if the drip chamber is not full enough, then air can enter into the IV tubing. From the tubing air could get into the patient's circulatory system (if the device is being used for IV delivery), which could potentially block a blood vessel or stop the heart.

Most IV medication or other fluids are ordered to infuse or deliver at a specific rate. Thus, the assembly is set up so that it infuses or delivers at this specific rate and to adjust the IV periodically if the actual rate deviates from the ordered rate. The rate at which a fluid infuses is referred to as the "IV infusion rate" or "flow rate." The roller clamp (40) (FIG. and FIG. 6) is the mechanism to control the rate at which the IV fluid infuses. If the roller clamp is rolled in a particular direction, it squeezes the IV tubing more tightly, making it narrower and therefore restricting the fluid flow through the tubing. And if the roller clamp is rolled in the opposite direction, it loosens its pinching of the IV tubing, making the tubing less narrow, and allowing the IV fluid to flow through at a faster rate. All roller clamps on a set of IV tubing should be closed before attaching a bag of IV fluid to the top of the tubing in order to ensure that no air gets into the tubing. The slide clamp (102) (FIG. 6) is used to completely stop the IV from flowing, without having to adjust the roller clamp. This feature is particularly useful if it is desired to momentarily stop the IV without having to readjust the roller clamp to its previous settings. The side clamp works by pinching the tubing completely shut when the tubing is slid into the narrowest part of the side clamp. Additional IV medication (s) can be delivered to a patient by methods that include, but are not limited to, adding the medications into the original IV bag and introducing the medications via the male luer lock injection site (104) and luer activated Y connector (106) disclosed in FIG. 6.

Alternatively or additionally, an injection port can be used to inject medicine or fluids other than those in the current IV bag into the patient's vein through the IV tubing. An injection port is a means by which medicine or fluids other than those in the IV bag can be injected or administered such that they will infuse into the patients vein (or into a target device) through the IV tubing. There are two possible port sites: one on the IV bag, itself (12) (FIG. 4) and one below the drip chamber (104) (FIG. 6). There may also be an injection port (106) FIG. 6 close to where the needle goes into the patient's vein. The injection port on the rv bag is used if medication mixing with the fluid in the IV bag is required. If the medication is injected into this port and the bag "rolled" to mix the medication with the fluid in the bag, then the patient will receive both the medication and the IV fluid simultaneously at the allocated drip rate. A second medication or fluid can be injected directly via injection port (106) (FIG. 6) so that it is not diluted with the IV fluid, then one of the ports that is located below the drip chamber is used.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A drip cup comprising:
   a drip cup upper half, at least a portion of which is made of a polymeric material, wherein the drip cup upper half includes a substantially hemispherical drip cup top having an upper portion that defines a chamber inlet and a lower portion comprising one of a circular male member and a circular female member, and a neck portion, one end of which is connected to and extending from the chamber inlet, and an opposite end of which defines a neck inlet in fluid communication with the chamber inlet, wherein the neck inlet comprises a neck inlet diameter, wherein the neck portion comprises a cap which covers the neck inlet, wherein the cap comprises a distal inlet configured to be connected to a source of fluid, and wherein a diameter of the distal inlet is smaller than the neck inlet diameter; and
   a drip cup lower half comprising a substantially hemispherical drip cup bottom at least a portion of which is formed of a rigid material, the drip cup bottom comprising a first portion defining a chamber outlet and a second portion including the other one of the circular male member or the circular female member, wherein the circular female member comprises an inner circular female portion and an outer circular female portion spaced apart from one another to receive the male member between the inner and outer circular female portions thereby joining the drip cup top to the drip cup bottom, wherein the first portion comprises a structure that includes the chamber outlet, the structure extending into an interior of the drip cup operatively positioning the chamber outlet substantially centrally within a spherical volume defined by the joined drip cup top and drip cup bottom such that the chamber outlet remains submerged in a fluid irrespective of orientation of the drip cup when the drip cup is filled to a predetermined level.

2. The drip cup of claim 1, wherein the polymeric material comprises a soft polymer, and wherein the rigid material comprises a rigid polymer.

3. The drip cup of claim 1, wherein the drip cup upper half further comprises a fill line that indicates the predetermined level.

4. The drip cup of claim 1, wherein the circular male member is further bonded, welded, molded, or glued to the circular female portion.

5. The drip cup of claim 1, wherein the drip cup upper half comprises the circular male member and the drip cup lower half comprises the circular female portion.

6. The drip cup of claim 1, wherein the neck portion is cylindrical.

7. The drip cup of claim 1 further comprising an automatically or manually sealable vent for purging air or other gas from the drip cup.

8. A drip cup comprising:
   an upper half comprising a substantially hemispherical drip cup top having an upper portion that defines a chamber inlet and a lower portion that includes one of a circular male member and a circular female member, the upper half further comprising a neck, one end of which is connected to and extending from the chamber inlet, and an opposite end of which defines a neck inlet in fluid communication with the chamber inlet, the neck inlet comprising a neck inlet diameter, wherein the neck comprises a cap that covers the neck inlet, wherein the cap comprises a distal inlet configured to be connected to a source of fluid, a diameter of the distal inlet of the cap being smaller than the neck inlet diameter; and
   a lower half comprising a substantially hemispherical drip cup bottom comprising a first portion that defines a chamber outlet and a second portion comprising the other one of the circular male member and the circular female member, wherein the circular female member comprises an inner circular female portion and an outer circular female portion spaced apart from one another to receive the male member between the inner and outer circular female portions thereby joining the drip cup top to the drip cup bottom, wherein the first portion comprises a structure that includes the chamber outlet, the structure extending into an interior of the drip cup operatively positioning the chamber outlet substantially centrally within a spherical volume defined by the joined drip cup top and drip cup bottom such that the chamber outlet remains submerged in fluid irrespective of orientation of the drip cup when the drip cup is filled with the fluid to a predetermined level.

9. The drip cup of claim 8, wherein the upper half comprises a squeezable material whereby the neck is operable to be squeezed for priming the drip cup.

10. The drip cup of claim 8, wherein the cap is formed separately from the neck and bonded to the neck to seal the neck inlet.

11. The drip cup of claim 8, wherein the chamber outlet extends into the interior of the drip cup such that it is positioned at a same elevation as the other one of the circular male member and the circular female member of the lower half.

12. The drip cup of claim 8 further comprising an automatically or manually sealable vent for purging air or other gas from the drip cup.

13. A system comprising the drip cup of claim 8 and a tube having a first end connected to the neck inlet for fluidly connecting a source of fluid to the neck inlet.

14. The system of claim 13 further comprising a spike at an end of the tube opposite the first end.

15. The system of claim 13, wherein the tube is a first tube, the system further comprising a second tube connected to the chamber outlet.

16. A method of using the system of claim 15, comprising:
connecting the spike to the source of fluid;
priming the drip cup with the fluid by providing the fluid into the interior of the drip cup through the first tube; and
supplying the fluid out of the drip cup by passing the fluid out of the chamber outlet and into the second tube.

17. The method of claim 16, wherein the source of fluid is a fluid bag, the method further comprising applying a pressure to the fluid bag.

18. A drip cup assembly comprising:
a drip chamber top comprising an upper portion defining a chamber inlet for receiving fluid into the drip chamber and a lower portion comprising one of a circular male member and a circular female member;
a neck portion comprising a first end connected to and extends from the chamber inlet, and a second opposite end defining a neck inlet in fluid communication with the chamber inlet, the neck inlet having a neck inlet diameter;
a drip chamber cap covering the neck inlet, wherein the drip chamber cap comprises a distal inlet configured to be connected to a source of fluid, the distal inlet having a diameter smaller than the neck inlet diameter; and
a drip chamber bottom comprising a lower portion defining a drip chamber outlet and an upper portion comprising the other one of the circular male member or the circular female member, the circular female member comprising an inner circular female portion and an outer circular female portion spaced apart from one another to accommodate insertion of the male member between the inner and outer portions of the female member to form a male-female joint that joins the drip chamber top to the drip chamber bottom, wherein the lower portion comprises a structure that includes the drip chamber outlet, the structure extending into an interior of the joined drip chamber top and bottom thereby positioning the drip chamber outlet at a substantially same distance from interior walls of the joined drip chamber top and bottom such that the chamber outlet remains submerged in the fluid irrespective of orientation of the drip chamber assembly when the drip chamber assembly is filled with fluid at least up to a fill level above the male-female joint of the drip chamber assembly.

19. The drip cup assembly of claim 18, wherein the neck portion is integrally formed with the drip chamber top.

20. The drip cup assembly of claim 19, wherein the drip chamber cap is separately formed from the drip chamber top.

21. A kit comprising the drip cup assembly of claim 20, and wherein the drip chamber cap is one of a plurality of caps with respective outlets having different cross-sectional areas to provide a different flow rate through the respective one of the plurality of caps.

22. The drip cup assembly of claim 18 further comprising an automatically or manually sealable vent for purging air or other gas from the drip cup.

\* \* \* \* \*